US008782142B2

(12) United States Patent
Swanson et al.

(10) Patent No.: US 8,782,142 B2
(45) Date of Patent: Jul. 15, 2014

(54) SYSTEM AND METHOD FOR EVALUATING HEALTHCARE INFORMATION TECHNOLOGY

(75) Inventors: Randy R. Swanson, Folsom, CA (US); Sunil Shah, Folsom, CA (US); Gregory Montemayor, Folsom, CA (US)

(73) Assignee: Intel Corporation, Santa Clara, CA (US)

( * ) Notice: Subject to any disclaimer, the term of this patent is extended or adjusted under 35 U.S.C. 154(b) by 1278 days.

(21) Appl. No.: 11/648,130

(22) Filed: Dec. 29, 2006

(65) Prior Publication Data

US 2008/0208619 A1   Aug. 28, 2008

(51) Int. Cl.
*G06F 15/16*   (2006.01)

(52) U.S. Cl.
USPC ........................................................ 709/206

(58) Field of Classification Search
USPC ................................................... 705/1, 2, 36
See application file for complete search history.

(56) References Cited

U.S. PATENT DOCUMENTS

| | | | | |
|---|---|---|---|---|
| 2005/0234794 A1* | 10/2005 | Melnicoff et al. | ............... | 705/36 |
| 2006/0229896 A1* | 10/2006 | Rosen et al. | ....................... | 705/1 |
| 2008/0015896 A1* | 1/2008 | Reynolds | .......................... | 705/2 |

OTHER PUBLICATIONS

Fonkych, et al., 2005. "The State and Pattern of Health Information Technology Adoption". http://www.rand.org/pubs/monographs/2005/RAND_MG409.pdf.
Schmidek, et al., 2005. "What do we know about Financial Returns on Investments in Patient Safety". Journal on Quality and Patient Safety 31(12): 690-699.
Johnston, et al., 2002. "Finding the Value in Healthcare Information Technologies". Center for IT Leadership, Partners's Healthcare, Boston, MA.

* cited by examiner

*Primary Examiner* — Valerie Lubin
(74) *Attorney, Agent, or Firm* — Pillsbury Winthrop Shaw Pittman LLP

(57) ABSTRACT

A method for evaluating a healthcare information system includes first determining a first specification for the healthcare information system. The first specifications may include healthcare profile data for specifying a profile of a healthcare provider, technology profile data for specifying a profile of technology resources, and performance data for measuring the benefits associated with performance indicators of the healthcare information system. Then, an evaluation is determined from the first specification, which may include system performance values. Additionally, characteristic values for performance indicators may be presented to the user. Next, a second specification is then determined by specifying to the user that at least some values of the first specification may be changed. Then, an evaluation for the healthcare information system is determined for the second specification.

29 Claims, 15 Drawing Sheets

| Hospital Profile | Assumption |
|---|---:|
| % of Annual Benefit Received in 1st Year | 50% |
| Admissions per bed | 30 |
| Number of Discharges | 4,500 |
| Revenue per Bed | $ 400,000 |
| Annual ED Visits per Bed | 200 |
| Physician Burdened Cost | $ 250,000 |
| Nurses Burdened Cost | $ 100,000 |
| Other Clinical staff Burdened Cost | $ 80,000 |
| Admin Staff Burdened Cost | $ 70,000 |
| IT Staff Burdened Cost | $ 125,000 |

402

| Solution Cost Estimation | Assumption |
|---|---:|
| Discount Rate | 15% |
| Number of IT Staff % of all other Users | 3% |
| Number of IT Staff | 9 |
| Number of Admin Users% of Clinical Staff | 5% |
| Number of Admin Users | 15 |
| Software License Cost per user | $ 7,500 |
| Cost per Desktop | $ 700 |
| Cost per Laptop/Tablet | $ 1,200 |
| Cost per Server | $ 4,000 |

Patient Safety — Assumption — 518
Staff Affected by ADEs — 150
Annual ADE Cost per Provider — $ 6,500 — 514
% fewer medication errors — 30%

Cost of Medication Claims per 1000 Admits — $ 15,000 — 516
% reduction in claims — 7%

504

Quality of Care — Assumption — 520
Average Cost Per Admission — $ 4,500
ALOS Reduction (in days) — 0.5
Cost per Admission avoided from reduced ALOS — $ 500
% more contribution margin from increased capacity — 11%
% growth from improved reputation — 0%
Estimated Cost of Quality/Regulatory Reporting — $ -
% reduction in reporting costs — 0%

506

Patient Satisfaction — Assumption
Average revenue per outpatient visit — $ 500
Estimated % of ED visitors leaving without being seen — 8%
Estimated # of ED visitors leaving without being seen — 2,400
Estimated improvement in ED visitors leaving without being seen — 5%

508

Staff Productivity — Assumption
Overtime expenditure per 1,000 admissions — $ 250,000
% reduction in overtime expenditure — 7%
Forms expenditure per 1000 Admissions — $ 20,000
% reduction in forms expenditure — 20%
Document storage and retrieval cost per 1000 Admissions — $ 2,500
% reduction in storage and retrieval costs — 80%

510

Staff Satisfaction — Assumption
Annual nurse turnover — 20%
Total cost of replacement per nurse — $ 40,000
% reduction in nurse turnover — 15%

512

Revenue Enhancement — Assumption
Current Days in A/R — 49
Value Day in AR — $ 166,667
Reduction in Days in A/R — 5
Gross Improvement in Cash Flow — $ 833,333
Opportunity Cost of Capital — 8%

Current volume of Elective Procedures/Bed — 15
Contribution Margin per Surgical Procedure — $ 5,000
% improvement in Elective Procedure Volume — 10%

514

Cost Optimization — Assumption
Drug expenditure per 1,000 Admissions — $ 500,000
% reduction in Drug Expenditure — 5%

*Figure 5A*

| Patient Safety | Assumption |
|---|---:|
| Staff Affected by ADEs | 150 |
| Annual ADE Cost per Provider | $ 6,500 |
| % fewer medication errors | 60% |
| | |
| Cost of Medication Claims per 1000 Admits | $ 15,000 |
| % reduction in claims | 7% |

540

| Quality of Care | Assumption |
|---|---:|
| Average Cost Per Admission | $ 4,500 |
| ALOS Reduction (in days) | 0.5 |
| Cost per Admission avoided from reduced ALOS | $ 500 |
| % more contribution margin from increased capacity | 11% |
| % growth from improved reputation | 0% |
| Estimated Cost of Quality/Regulatory Reporting | $ - |
| % reduction in reporting costs | 0% |

| Patient Satisfaction | Assumption |
|---|---:|
| Average revenue per outpatient visit | $ 500 |
| Estimated % of ED visitors leaving without being seen | 8% |
| Estimated # of ED visitors leaving without being seen | 2,400 |
| Estimated improvement in ED visitors leaving without being seen | 5% |

| Staff Productivity | Assumption |
|---|---:|
| Overtime expenditure per 1,000 admissions | $ 250,000 |
| % reduction in overtime expenditure | 7% |
| Forms expenditure per 1000 Admissions | $ 20,000 |
| % reduction in forms expenditure | 20% |
| Document storage and retrieval cost per 1000 Admissions | $ 2,500 |
| % reduction in storage and retrieval costs | 80% |

| Staff Satisfaction | Assumption |
|---|---:|
| Annual nurse turnover | 20% |
| Total cost of replacement per nurse | $ 40,000 |
| % reduction in nurse turnover | 15% |

| Revenue Enhancement | Assumption |
|---|---:|
| Current Days in A/R | 49 |
| Value Day in AR | $ 166,667 |
| Reduction in Days in A/R | 5 |
| Gross Improvement in Cash Flow | $ 833,333 |
| Opportunity Cost of Capital | 8% |
| | |
| Current volume of Elective Procedures/Bed | 15 |
| Contribution Margin per Surgical Procedure | $ 5,000 |
| % improvement in Elective Procedure Volume | 10% |

| Cost Optimization | Assumption |
|---|---:|
| Drug expenditure per 1,000 Admissions | $ 500,000 |
| % reduction in Drug Expenditure | 5% |

| Hospital Profile | | Result |
|---|---|---|
| Annual Number of Patient Days | | 20,250 |
| Occupancy Rate | | 37% |
| Patient Days per bed | | 135 |
| Revenue per Bed | $ | 400,000 |
| Revenue per Admission | $ | 13,333 |
| Annual Admissions Per Bed | | 30 |

704

| Solution Cost Estimation | | Input |
|---|---|---|
| Initial Cost of Desktops | $ | 105,000 |
| Initial Cost of Laptops/Tablets | $ | 191,340 |
| Initial Cost of Servers | $ | 61,890 |
| Initial Services Cost | $ | 51,640 |
| Ongoing Software Cost | $ | 608,344 |
| Ongoing Services Cost | $ | 51,640 |
| Ongoing Harware Cost | $ | 121,660 |

706

| Patient Safety: Fewer Adverse Drug Events | | Result |
|---|---|---|
| *Digital information can improve patient safety through avoidance of ADEs from prescription to dispensing* | | |
| Estimated Cost of ADEs | $ | 975,000 |
| % fewer medication errors | | 30% |
| Annual Benefit from Fewer Medication Errors | $ | 292,500 |

710

708

| Patient Safety: Fewer Medication-related Legal Claims | | Result |
|---|---|---|
| *Improved patient safety result in fewer medical malpractice claims and potentially lower related insurance costs* | | |
| Cost of Malpractice Claims | $ | 67,500 |
| % fewer claims | | 7% |
| Annual Benefit from Fewer Malpractice Claims | $ | 4,725 |

| QoC: Cost Savings from Better Care | | Result |
|---|---|---|
| Improved QoC can reduce the average length of stay thereby avoiding costs | | |
| Annual Admissions | | 4,500 |
| ALOS Reduction (in days) | | 0.5 |
| Benefit of Cost Avoidance | $ | 1,125,000 |
| Benefit of Increased capacity | $ | 981,481 |
| *Annual Benefit from Shorter LOS* | $ | *2,106,481* |

804

| QoC: Revenue Improvement | | Result |
|---|---|---|
| Quality reputation can grow business | | |
| Contribution Margin per Admission | $ | 1,963 |
| Incremental Growth | | 0.0% |
| *Annual Benefit from Net Income Reputation Improvement* | $ | - |

806

| QoC: Cost Savings from Reporting | | Result |
|---|---|---|
| By being easier to read, transfer, and store, digital information can improve reporting associated with quality of care | | |
| Estimated Cost of Quality/Regulatory Reporting | $ | - |
| % savings from improved documentation | | 0% |
| *QoC: Cost Savings from Reporting* | $ | - |

808

| Patient Satisfaction: Fewer Patients Leaving w/o Being Seen | | Result |
|---|---|---|
| IT can improve emergency department productivity resulting in improved patient access | | |
| Lost revenue from ED visitors leaving w/o being seen | $ | 1,200,000 |
| More ED visitors Treated | | 5% |
| *Annual Benefit from treating more ED visitors* | $ | *60,000* |

| Staff Productivity: Less Overtime Expenditure | | Result |
|---|---|---|
| IT can improve the productivity of administrative and clinical staff for activities associated documentation and chart reviews | | |
| Overtime expenditure per 1,000 admissions | $ | 250,000 |
| % reduction in overtime expenditure | | 7% |
| Annual Benefit from less overtime expenditure | $ | 78,750 |

904

| Staff Productivity: Lower cost of managing paper | | Result |
|---|---|---|
| Digital information reduces the need to purchase and store paper | | |
| Forms expenditure per 1000 Admissions | $ | 20,000 |
| % reduction in forms expenditure | | 20% |
| Document storage and retrieval cost per 1000 Admissions | $ | 2,500 |
| % reduction in storage and retrieval costs | | 80% |
| Annual Benefit from the lower cost of managing paper | $ | 27,000 |

906

| Staff Satisfaction: Lower staff replacement costs | | Result |
|---|---|---|
| IT can improve the satisfaction of administrative and clinical staff by enabling them to spend less time performing administrative activities and for time with patients | | |
| Less nurse turnover | | 15% |
| Total cost of replacement per nurse | $ | 40,000 |
| Annual Benefit from reducing nurse turnover | $ | 120,000 |

908

| Revenue Enhancement: Lower days in A/R | | Result |
|---|---|---|
| IT and revenue cycle management may reduce the time from performance of services to cash collection | | |
| Reduction in Days in A/R | | 5.0 |
| Gross Improvement in Cash Flow | $ | 833,333 |
| Opportunity Cost of Capital | | 8% |
| Annual Benefit from fewer days in A/R | $ | 66,667 |

910

| Revenue Enhancement: Value from more elective procedures | | Result |
|---|---|---|
| IT can improve scheduling and facility utilization by increasing the volume of elective procedures | | |
| Current volume of Elective Procedures/Bed | | 15.0 |
| Contribution Margin per Surgical Procedure | $ | 5,000 |
| % improvement in Elective Procedure Volume | | 10% |
| Annual Benefit from Greater Volume of Elective Procedures | $ | 1,125,000 |

912

| Cost Optimization: Value from lower drug expenditures | | Result |
|---|---|---|
| IT can improve pharmaceutical purchasing and prescribing resulting in lower overall expenditure | | |
| Drug expenditure per 1,000 Admissions | $ | 500,000 |
| % reduction in Drug Expenditure | | 5% |
| Annual Benefit from Lower Drug Expenditures | $ | 112,500 |

COST CALCULATIONS

| Initial Investment | Year 0 |
|---|---|
| Software | $ (2,433,375) |
| Services | $ (264,560) |
| Hardware | $ (364,980) |
| Total Initial Costs | $ (3,062,915) |

| | Year | | | | | | | |
|---|---|---|---|---|---|---|---|---|
| Ongoing Costs | 0 | 1 | 2 | 3 | 4 | 5 | 6 | 7 |
| Software | | $ (608,344) | $ (608,344) | $ (608,344) | $ (608,344) | $ (608,344) | $ (608,344) | $ (608,344) |
| Services | | $ (51,640) | $ (51,640) | $ (51,640) | $ (51,640) | $ (51,640) | $ (51,640) | $ (51,640) |
| Hardware | | $ (121,660) | $ (121,660) | $ (121,660) | $ (121,660) | $ (121,660) | $ (121,660) | $ (121,660) |
| Total Ongoing Costs | | $ (781,643) | $ (781,643) | $ (781,643) | $ (781,643) | $ (781,643) | $ (781,643) | $ (781,643) |
| PV of all Costs | $ (3,062,915) | $ (679,690) | $ (591,035) | $ (513,943) | $ (446,907) | $ (388,615) | $ (337,926) | $ (293,849) |
| Cumulative Costs | $ 3,062,915 | $ 3,844,558 | $ 4,626,202 | $ 5,407,845 | $ 6,189,489 | $ 6,971,132 | $ 7,752,776 | $ 8,534,419 |

1104

BENEFIT CALCULATIONS

| | Year | | | | | | | |
|---|---|---|---|---|---|---|---|---|
| Benefits | 0 | 1 | 2 | 3 | 4 | 5 | 6 | 7 |
| Patient Safety | | $ 148,613 | $ 297,225 | $ 297,225 | $ 297,225 | $ 297,225 | $ 297,225 | $ 297,225 |
| Quality of Care | | $ 1,053,241 | $ 2,106,481 | $ 2,106,481 | $ 2,106,481 | $ 2,106,481 | $ 2,106,481 | $ 2,106,481 |
| Patient Satisfaction | | $ 30,000 | $ 60,000 | $ 60,000 | $ 60,000 | $ 60,000 | $ 60,000 | $ 60,000 |
| Staff Productivity | | $ 52,875 | $ 105,750 | $ 105,750 | $ 105,750 | $ 105,750 | $ 105,750 | $ 105,750 |
| Employee Satisfaction | | $ 60,000 | $ 120,000 | $ 120,000 | $ 120,000 | $ 120,000 | $ 120,000 | $ 120,000 |
| Revenue Enhancement | | $ 595,833 | $ 1,191,667 | $ 1,191,667 | $ 1,191,667 | $ 1,191,667 | $ 1,191,667 | $ 1,191,667 |
| Cost Optimization | | $ 56,250 | $ 112,500 | $ 112,500 | $ 112,500 | $ 112,500 | $ 112,500 | $ 112,500 |
| Total Benefits | $ - | $ 1,996,812 | $ 3,993,623 | $ 3,993,623 | $ 3,993,623 | $ 3,993,623 | $ 3,993,623 | $ 3,993,623 |
| PV of Benefits | $ - | $ 1,736,358 | $ 3,019,753 | $ 2,625,872 | $ 2,283,367 | $ 1,985,537 | $ 1,726,553 | $ 1,501,351 |
| Ramp of Benefits | | 50% | 100% | 100% | 100% | 100% | 100% | 100% |
| Cumulative Benefits | $ - | $ 1,996,812 | $ 5,990,435 | $ 9,984,058 | $ 13,977,681 | $ 17,971,304 | $ 21,964,927 | $ 25,958,550 |

| | | | | | RETURNS CALCULATIONS | | | |
|---|---|---|---|---|---|---|---|---|
| Net Benefits | $ (3,062,915) | $ 1,215,168 | $ 3,211,980 | $ 3,211,980 | $ 3,211,980 | $ 3,211,980 | $ 3,211,980 | $ 3,211,980 |
| Discount Rate | 15% | 15% | 15% | 15% | 15% | 15% | 15% | 15% |
| PV of Net Benefits | $ (3,062,915) | $ 1,056,668 | $ 2,428,718 | $ 2,111,929 | $ 1,836,460 | $ 1,596,922 | $ 1,388,627 | $ 1,207,502 |

1204

| Net Present Value | $ (3,062,915) | $ (2,006,247) | $ 422,471 | $ 2,534,400 | $ 4,370,860 | $ 5,967,781 | $ 7,356,409 | $ 8,563,911 |
|---|---|---|---|---|---|---|---|---|

| | | | | | Year | | | |
|---|---|---|---|---|---|---|---|---|
| | 0 | 1 | 2 | 3 | 4 | 5 | 6 | 7 |
| Value of Benefit | $ - | $ 1,996,812 | $ 5,990,435 | $ 9,984,058 | $ 13,977,681 | $ 17,971,304 | $ 21,964,927 | $ 25,958,550 |
| Value of Investment | $ (3,062,915) | $ (3,844,558) | $ (4,626,202) | $ (5,407,845) | $ (6,189,489) | $ (6,971,132) | $ (7,752,776) | $ (8,534,419) |
| ROI % | 0% | 52% | 129% | 185% | 226% | 258% | 283% | 304% |

1206

1208

| IRR | NA | NA | 24% | 53% | 65% | 71% | 73% | 75% |
|---|---|---|---|---|---|---|---|---|

| Payback Period | | | | 2.86 | | | | |
|---|---|---|---|---|---|---|---|---|

*Figure 12*

SYSTEM AND METHOD FOR EVALUATING HEALTHCARE INFORMATION TECHNOLOGY

BACKGROUND OF THE INVENTION

1. Field of Invention

The present invention relates to evaluating information technology and more particularly to measuring the effect of information technology on the healthcare industry.

2. Description of Related Art

Understanding the tradeoffs between the costs of information technology (IT) and the benefits of improved healthcare requires a detailed understanding of both subjects as well as their interrelationships. See, for example: Fonkych, Kateryna et al., "The State and Pattern of Health Information Technology Adoption", Rand Health, 2005; Schmidek, Jared M., et al., "What do we know about Financial Returns on Investments in Patient Safety", *Journal on Quality and Patient Safety*, Volume 31 Number 12, December 2005, pp. 690-699; and Johnston, Doug, et al., "Finding the Value in Healthcare Information Technologies", Center for IT Leadership, Partners Healthcare, Boston, Mass., 2002, each of which is herein incorporated by reference in its entirety.

There are many examples of IT improving efficiency and quality across many industries. However, the healthcare industry is relatively short of success stories. This is mainly due to the relatively low levels of adoption by the industry. The healthcare industry allocates a smaller percentage of revenue to IT than most other industries. This is indicative of the perception of IT is in the healthcare industry and the realities that a Chief Information Officer in healthcare may cope with. The year-over-year increases in IT investments are a clear demonstration that the perception of IT is slowly shifting from that of cost center to care delivery partner. Technology is seen as a solution, if only in part, to many healthcare business imperatives including: legislative compliance, cash flow, reimbursement levels, staffing shortages and staff workload, inefficient business processes, medical outcomes and most importantly, reducing preventable medical errors. The reduction of medical errors continues to be a top priority for healthcare worldwide.

Advances in IT provide great potential for yielding positive changes for patients, healthcare providers and payers by enabling access to the right information, for the right people at the right time. By providing clinicians with faster access to patient data and clinical decision support, IT enables increased patient safety and improves the overall quality of care. The benefits of IT also include: (a) improved access to care from streamlined processes; (b) integration of traditionally disparate patient and administrative information; (c) increased productivity and job satisfaction for clinical staff; (d) faster patient throughput and shorter waiting times; and (e) reduced administrative costs and (f) other forms of cost savings such as lower reporting and inventory costs.

However, there is a scarcity of rigorous studies to prove the value of actual Healthcare IT (HIT) implementations. Therefore, there is very little hard evidence demonstrating the value of specific HIT investments. Ideally, a useful study of HIT value is one that captures all of the benefits—both tangible and intangible—and provides sufficient evidence to drive effective HIT decision making. Then, better data about the value of HIT can enable healthcare providers to improve their investment decisions. However, there is generally a lack of information about the true costs, benefits and experience associated with Healthcare IT investments. The resulting uncertainty is a major barrier to adoption especially when the competition for investment funding is tight and operating margins at most health care organizations are shrinking.

Thus, there is a need for an approach to a comprehensive understanding and evaluation of the benefits of HIT adoption for improved evaluation of healthcare information technology.

BRIEF DESCRIPTION OF THE DRAWINGS

FIG. 4 shows exemplary assumptions for a healthcare profile and a technology profile according to an embodiment of the present invention.

FIG. 5A shows exemplary assumptions for healthcare drivers and associated performance indicators for a specification according to an embodiment of the present invention.

FIG. 5B shows exemplary assumptions for healthcare drivers and associated performance indicators for a second specification according to an embodiment of the present invention.

FIG. 7 shows an exemplary evaluation of a specification according to IT impact on the healthcare industry according to an embodiment of the present invention.

FIG. 8 shows an exemplary evaluation of a specification according to IT impact on the healthcare industry according to an embodiment of the present invention.

FIG. 9 shows an exemplary evaluation of a specification according IT impact on the healthcare industry according to an embodiment of the present invention.

FIG. 11 shows exemplary annual cost and benefit calculations of an evaluation according to an embodiment of the present invention.

FIG. 12 shows exemplary annual return calculations, net present values (NPV), return on investment (ROI), and internal rate of return (IRR) of an evaluation according to an embodiment of the present invention.

DETAILED DESCRIPTION OF EXEMPLARY EMBODIMENTS

In one embodiment of the present invention, a method for evaluating a healthcare information system includes determining a first specification for the healthcare information system. The first specification may include healthcare profile data for specifying a profile of a healthcare provider, technology profile data for specifying a profile of technology resources, and performance data for measuring the benefits associated with performance indicators of the healthcare information system. Then, an evaluation is determined from the first specification, which may include system performance values. Additionally, characteristic values for performance indicators may be presented to the user. Next, a second specification is then determined by specifying at least some values of the first specification may be adjusted. Then, an evaluation for the healthcare information system is determined for the second specification.

According to one aspect of this embodiment, the method may further include determining a plurality of healthcare drivers that characterize qualitative goals of the healthcare information system. Performance indicators may then be associated with a corresponding healthcare driver.

Additional embodiments relate to an apparatus for carrying out any one of the above-described methods, where the apparatus may include a computer for executing instructions related to the method. For example, the computer may include a processor with memory for executing at least some of the instructions. Additionally or alternatively the computer may include circuitry or other specialized hardware for executing at least some of the instructions. Additional embodiments also relate to a computer-readable medium that stores (e.g., tangibly embodies) a computer program for carrying out any one of the above-described methods with a computer.

In these ways the present invention enables improved evaluation of the benefits of healthcare information technology.

Evaluating IT Impact on the Healthcare Industry

Figure 1:
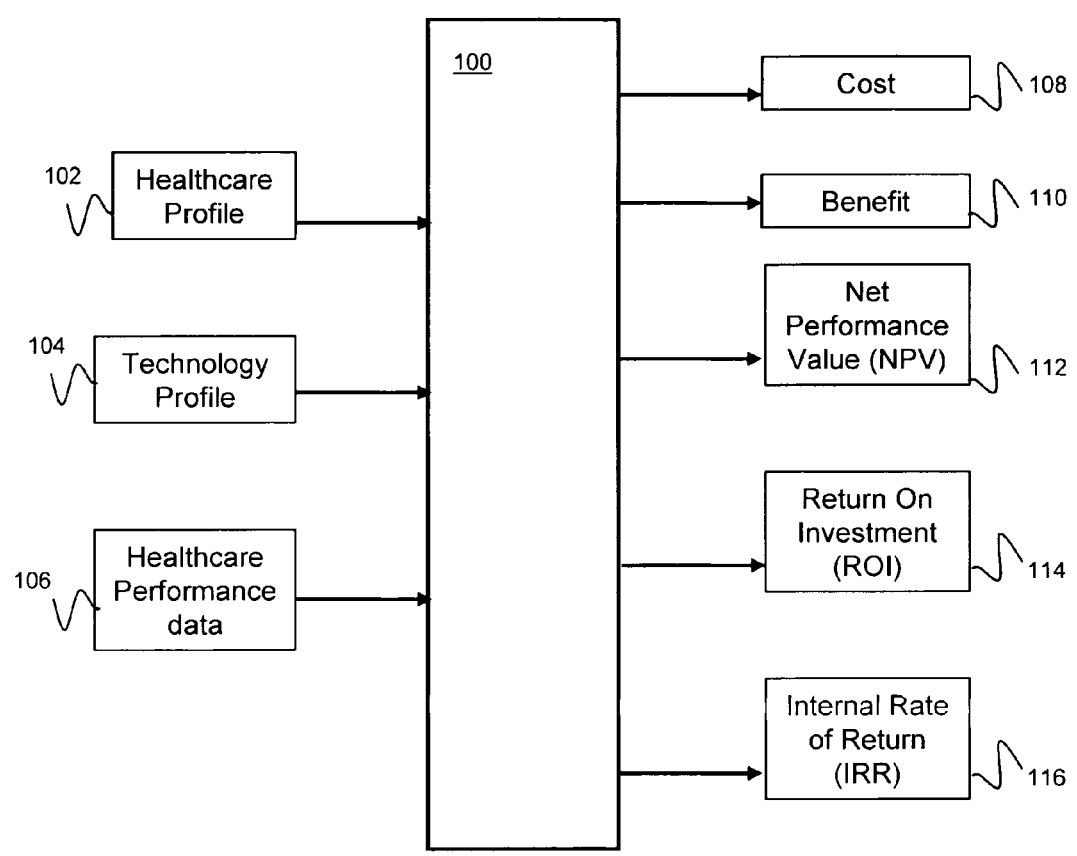
FIG. 1 shows exemplary inputs/outputs of an evaluation of IT impact on the healthcare industry according to an embodiment of the present invention.

An embodiment of the present invention is shown in FIG. 1. A system 100 for evaluating the benefits associated with healthcare information technology is illustrated. Inputs into system 100 may include a healthcare profile 102, a technology profile 104, and a healthcare performance database 106. The healthcare profile 102 and the technology profile 104 may include both input values and assumption values. The healthcare performance database may include a facility storage for performance indicator data and a HIT storage for performance data. The performance data 106 may include IT impact values for measuring the benefits associated with a healthcare information system. Outputs of system 100 may include the cost 108, the benefit 110, the net present value (NPV) 112, the return on investment (ROI) 114, and an internal rate of return (IRR) 116. The system 100 can be used in the application of the following method.

Figure 2:
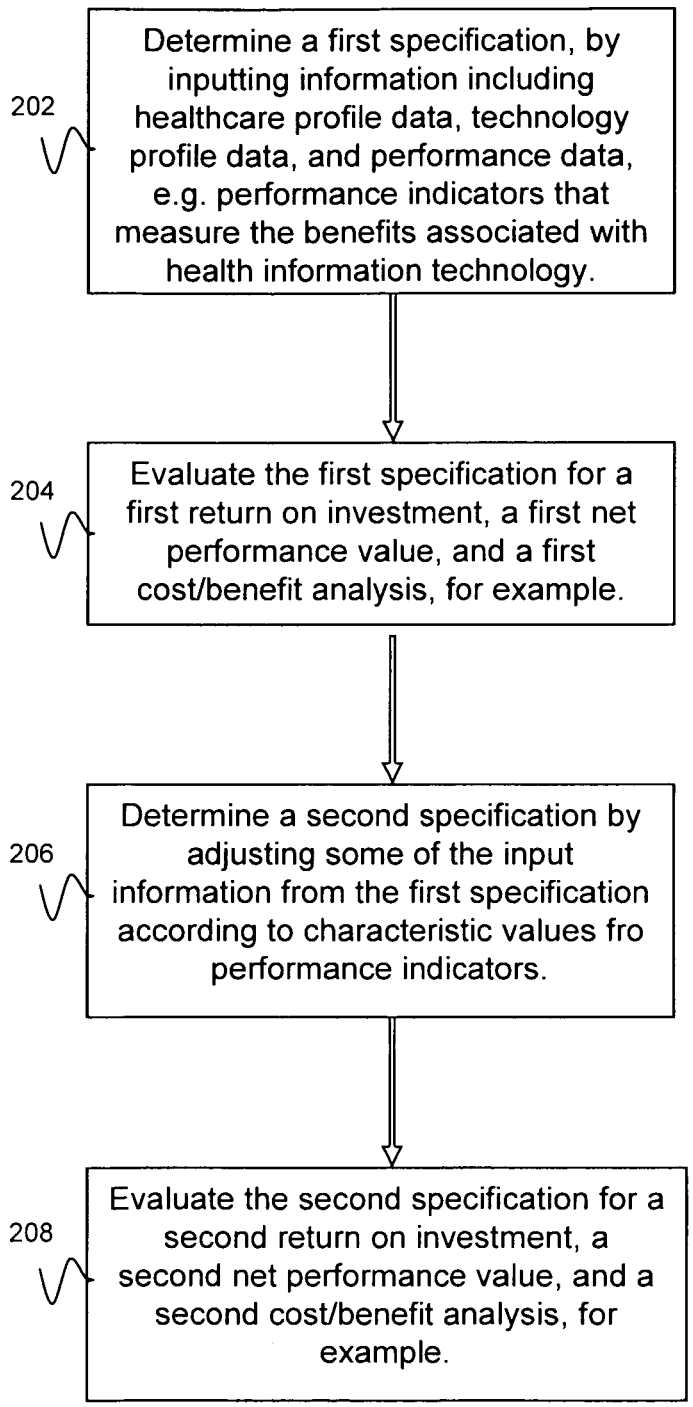
FIG. 2 shows a method for evaluating IT impact on the healthcare industry according to an embodiment of the present invention.

A method 200 for evaluating the benefits associated with healthcare information technology associated with system 100 is illustrated in FIG. 2. A first specification is determined in step 202. The first specification may include healthcare profile data specifying a profile of a healthcare provider, a technology profile data for specifying a profile of technology resources, and performance data for measuring benefits associated with performance indicators of the healthcare information system. In step 204, the first specification is evaluated for an evaluation that may include a cost benefit analysis, a ROI, an IRR, and a NPV. A second specification is determined as illustrated in step 206. Characteristic values, such as a range, may be indicated to the user for some performance indicators for customizing the first specification. Characteristic values may be from a healthcare performance database, which may have been compiled from at least one case study from a scientific journal, for example. Performance indicators indicate benefits associated with IT as applied to the healthcare industry. The second specification is evaluated in step 208 to show the customized evaluation of IT benefits according to the customized performance indicators and performance data. The evaluation may include cost/benefit analysis, a ROI, an IRR, and a NPV.

Note that although only a "first" specification and "second" specification are specified above, the present invention can be applied to any number of specifications. Also, note that the words "first" and "second" are used here and elsewhere for labeling purposes only and are not intended to denote any spatial or temporal ordering. Furthermore, the labeling of a "first" element does not imply the presence a "second" element.

Healthcare Profile and Technology Profile Inputs/Assumptions

Figure 3:
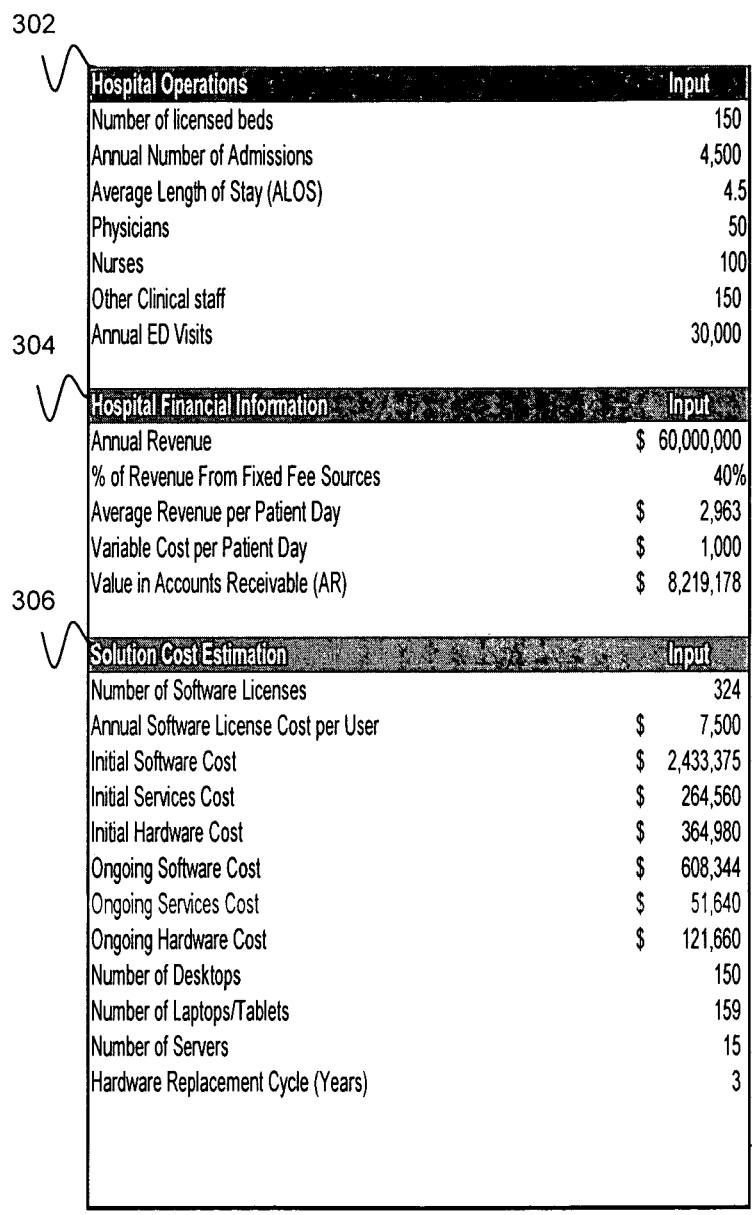
FIG. 3 shows exemplary inputs for a healthcare profile and a technology profile according to an embodiment of the present invention.

Exemplary healthcare profile inputs and technology profile inputs, included in the healthcare profile 102 and the technology profile 104, are illustrated in FIG. 3. Healthcare profile data inputs and technology profile data inputs may be included in a specification. The values in the healthcare profile data and the technology profile data may be input by the user or calculated based on some user input values. The healthcare profile data may include values related to hospital operations 302 and values related to the hospital financial information 304. The technology profile data may include values related to a solution cost estimation 306. A solution cost estimation 306 includes the estimated costs associated with an IT system, such as cost of software licenses, desktops, laptops, and servers. The values may be determined by vendor prices and adjusted according to the hospital needs. The healthcare profile inputs and technology profile inputs may be adjusted for customization in a second specification.

Exemplary healthcare profile data assumptions and technology profile data assumptions, included in the healthcare profile 102 and the technology profile 104, are illustrated in FIG. 4. The healthcare profile data assumptions and technology profile data assumptions may be included in a specification. The healthcare profile data may include assumption values associated with the hospital profile 402. The technology profile data may include assumption values related to a solution cost estimation 404. Assumption values related to the healthcare profile data and the technology profile data may be adjusted and customized.

Performance Data Inputs/Assumptions

Assumptions related to healthcare drivers and respective performance indicators, and associated performance data 106 for evaluating the benefits associated with healthcare information technology are illustrated in FIG. 5A. Performance data 106 may be included as data in the specification to be evaluated. In this embodiment, healthcare drivers include patient safety 502, quality of care 504, patient satisfaction 506, staff productivity 508, staff satisfaction 510, revenue enhancement 512, and cost optimization 514. Performance indicators for each healthcare driver reflect characteristic aspects that may have a significant impact on healthcare drivers. In general, a performance indicator provides a quantitative characterization of a corresponding healthcare driver. For example, a performance indicator under the healthcare driver patient safety may be the value of staff affected by ADEs (Adverse Drug Events) 518, and a performance indicator under the healthcare driver quality of care may be the value of average cost of admission 520. Also categorized with the healthcare drivers are performance data, which indicate IT impact on the performance indicator. The performance data values indicate how these are typically measured and the category indicates whether these are quantifiable (in monetary terms), measurable or intrinsic. Default, or nominal, values may be displayed to the user initially.

As illustrated in FIG. 5A, the performance data value of percent fewer medication errors 514 in the healthcare driver patient safety, shows a value of 30%. A user, for example, in a mouseover event (e.g., when a user moves the mouse cursor over the cell value), may be presented with a characteristic value range of 15-70%. The user may use the suggested range of characteristic values for the percent fewer medication errors from a performance database to form a second specification as in step 206, and as illustrated in FIG. 5B. A second performance data value of percent reduction in claims 516 under the healthcare driver patient safety, may include a characteristic value range of 5-10%, which also may be included in the performance database. The user may optimize the second specification by adjusting some performance data values to improve the values presented in the evaluation. The user may choose to use the characteristic value range as a suggestion for customization. Assumptions related to healthcare drivers and respective performance indicators may be included in a specification.

The performance database may include performance data 106, such as characteristic values for performance indicators. The performance data may include data from at least one case study, or may include compiled data from a plurality of case studies from a plurality of reference sources. The case studies may be from research presented in scientific journals, for example. Additionally, the performance database may include statistics including a maximum, minimum, or average value for performance indicators that the user may use in determining a specification. The performance database may also provide the user with values for performance indicators that correspond to other healthcare providers with similar profiles. In this way, the user may tailor performance indicators to compare evaluations of a first and a second specification.

Figure 6A:
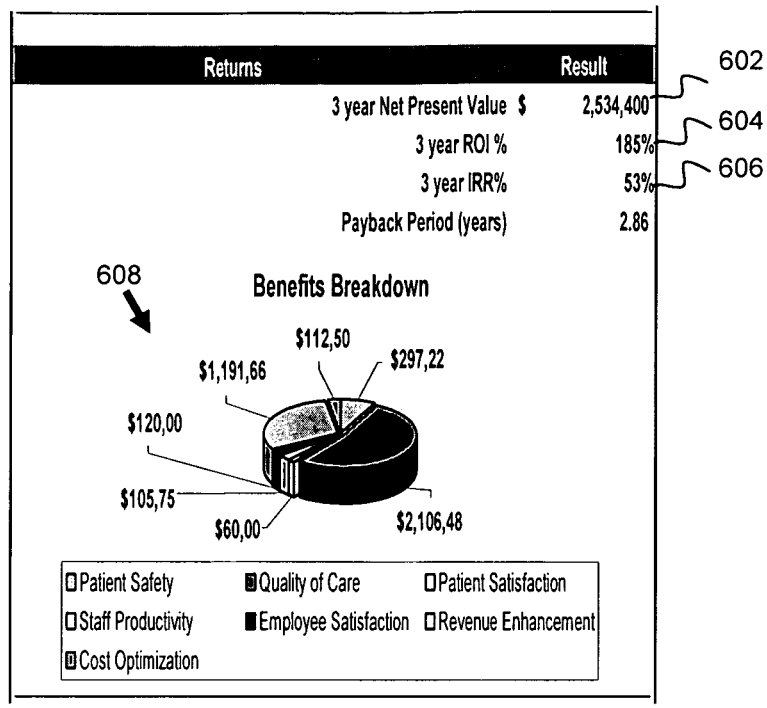
FIG. 6A shows an exemplary graphical presentation of an evaluation of a specification according to IT impact according to an embodiment of the present invention.
Figure 6B:
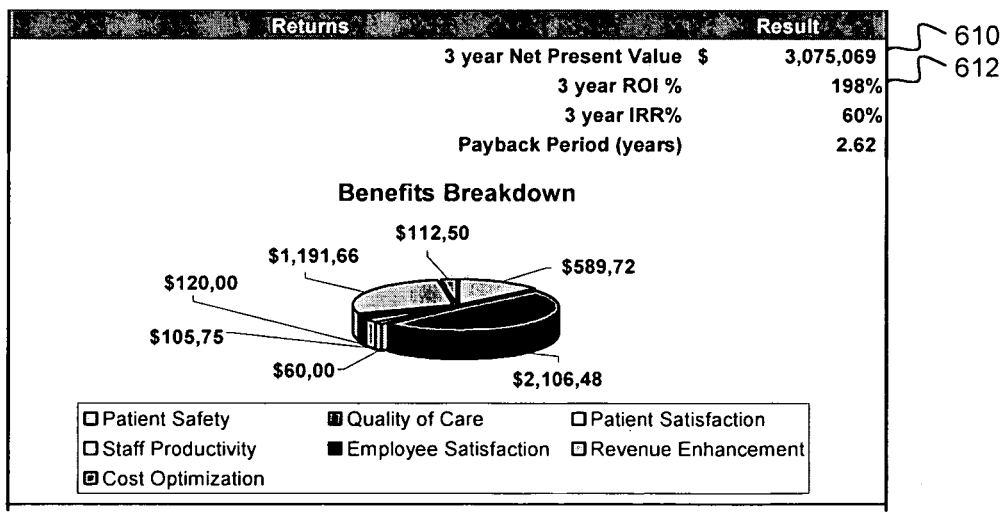
FIG. 6B shows an exemplary graphical presentation of an evaluation of a second specification according to IT impact according to an embodiment of the present invention.

For example, the healthcare provider with a certain technology profile may have 30% fewer medication errors 514 as a first specification, as illustrated in FIG. 5A. The first specification is evaluated as in step 204 in method 200, and presents a 3-year ROI percentage is 185% 604, as illustrated in FIG. 6A. Then, the technology profile is adjusted as in step 206, to form a second specification, as illustrated in FIG. 5B, so that the healthcare provider may now have 60% fewer medication errors. Now, the evaluation of the second specification, step 208, shows that the 3-year ROI percentage is 198% 612, with reference to FIG. 6B.

Examples of Healthcare Drivers

As discussed in the descriptions of FIG. 1, FIG. 2, FIG. 5A, and FIG. 5B, performance data may be categorized into healthcare drivers. Examples of healthcare drivers are: (1) Patient Safety—adherence to clinical protocols and improvements in the stages of clinical decision-making (i.e., initiation, diagnostics, monitoring and tracking, and acting) and clinical outcomes improvements represented as reductions in medical errors, decreases in morbidity and mortality, and expedited recovery times; (2) Quality of Care—creating a more positive perception of quality of care and clinician efficiency; (3) Patient Access—increasing stakeholder satisfaction from reduced wait times, improved access to healthcare information; (4) Labor Productivity—increased productivity of clinician staff through reducing administrative overhead such as paperwork; (5) Staff Satisfaction; (6) Revenue Enhancement—resulting from improved charge—capture and charge entry to billing times; and (7) Cost Optimization—such as cost reductions from decreased administrative clinical staffing and resource requirements (i.e. elimination of paper chart pulls and transcription services). The discussion below relates qualitative aspects of the healthcare drivers to quantitative evaluation by performance indicators. Examples of performance indicators are described below. However, quantitative evaluation is not limited to the performance indicators examples described.

1. Patient Safety

Patient safety concerns the avoidance of accidental injury while receiving medical care. In particular, patient safety refers to adverse events resulting from the most common medical errors—surgical and medication errors that result in direct hardship to the patient. The U.S. Institute of Medicine defines medical error as "the failure to complete a planned action as intended or the use of a wrong plan to achieve an aim." An adverse event refers to "an injury caused by medical management rather than by the underlying disease or condition of the patient." Surgical error often includes wrong site surgeries involving the wrong body part or even on the wrong patient. Medication errors involve wrong prescriptions or dosages that lead to adverse drug events. Other types of medical error include: misdiagnosis, misinterpretation of test results or medical orders, failure to act, equipment failure, and blood transfusion-related injuries.

The impact of medical error is significant. The U.S. Institute of Medicine, an arm of the National Academy of Sciences, estimates that as many as 98,000 U.S. patients die annually from preventable medical errors and it is the $8^{th}$ leading cause of death in the US. Of the deaths from medical error, the research indicates that 70% were preventable. According to previous studies, 40% of outpatient prescriptions are unnecessary, and patients receive only 55% of recommended care. In other reports, it was stated that 10% of hospital in-patient admissions may result in some kind of adverse event and that 18% of patients reported being the victim of a medication error some time in the previous two years. In terms of the economic impact, the Institute of Medicine estimates that medical error could add up to over $25 billion to US medical bills. Of particular concern in the US are medical malpractice costs which could comprise up to 29% of practice revenue according to one congressional report.

Healthcare providers are largely concerned with ways to reduce medical error and lower the occurrence of preventable adverse events that lead to death and injury. Non-lethal errors tend to lead to longer stays and otherwise avoidable treatments. The resulting increased expenditures from medical errors constitute avoidable costs that, at least in the US system, may not be reimbursable. Healthcare providers are concerned with being able to perform effective diagnosis and treatment selection. Healthcare providers typically measure prescription errors, surgical errors, transfusion errors and the number of professional liability claims.

Examples of performance indicators in IT benefit calculations associated with patient safety are adverse drug events (ADE) avoidance, and medication-related claims avoidance. These performance indicators may be calculated in a variety of ways.

For example, Adverse drug events (ADE) avoidance can be calculated as follows: (performance data associated with ADEs)×(therapy changes per 1000 acute admissions)×(total number of acute admissions/1000). In this example, "performance data associated with ADEs" is an improvement factor that relates IT with ADEs, and can be extracted from the performance database (e.g., from a case study). Additionally, "therapy changes per 1000 acute admissions" and "total number of acute admissions/1000", are normalized characteristic values that can be extracted from the healthcare profile 102.

Similarly, in another example, medication-related claims avoidance can be calculated as follows: (performance data associated with medication-related claims)×(medication-related claims cost per 1000 acute admissions)×(total number of acute admissions/1000). In this example, "performance data associated with medication-related claims" is an improvement factor that relates IT with medication-related claims, and can be extracted from the performance database (e.g., from a case study). Additionally, "medication-related claims cost per 1000 acute admissions" and "total number of acute admissions/1000" are normalized characteristic values that can be extracted from the healthcare profile 102.

2. Quality of Care

Quality of care as measured in part by patient satisfaction may be an important healthcare driver because of the inclusion of care metrics. Patient-centered care means providing care that is respectful of and responsive to individual patient preferences, needs, and values and ensuring that patient values guide all clinical decisions.

According to studies, the degree to which health services increase the likelihood of desired health outcomes and are consistent with current knowledge. Quality healthcare is largely associated with delivering the right care, at the right time, at the right place and in the right way as to achieve the best possible results. Providing quality healthcare involves striking the right balance of services by: (a) avoiding underuse (for example, not running a certain test); (b) avoiding overuse including performing tests that patients do not need; and (c) eliminating misuse involving care that may have harmful effects such as medication error.

Quality of care also includes: care coordination, improve doctor/patient relationship, provision of patient history and medical records, information/education/continuity, family involvement, physical comfort, emotional support, physical and nurse interface, special needs, would they return if ill again and administrative overhead and cost.

Many publications by healthcare quality organizations discuss measures to assess and track the quality of care provision. These healthcare quality organizations provide best practices and measures for treating conditions spanning acute conditions like heart attack and pneumonia to guidelines for surgical infection prevention, immunizations, and even preventive care. Tracking the alignment of the delivery of care to quality measures, as well as related health outcomes is growing in importance as the choices and decisions of consumers, payers, and even governments may be influenced by indicators of a provider's quality of care.

Access to the relevant patient details from any computer anywhere in the hospital 24 hours per day, greatly reduces the amount of time spent searching for Patient details, test results and the making and receiving of telephone enquiries. This allows more nursing time to be spent with patients thus positively impacting upon the quality of the patient care offered. Nurses, on average, spend two and a half hours per day on paperwork. Information technology record systems have proved this can be reduced to half an hour. The longer people stay in hospital the more dissatisfied they become. By administering the appropriate treatment earlier, this has impacted upon the patient's ability to recover more quickly and to be in a position to be released more timely. Reduced waiting times, elimination of repeat questioning and reduced readmissions are also aspects of quality of care.

An example of a performance indicator IT benefit calculations associated with the quality of care is an average length of stay (ALOS) reduction. This may be calculated in a variety of ways.

For example, ALOS reduction can be calculated by: (performance data associated with ALOS)×($ALOS_{considering\ DRG\ MIX}$)×(Average variable cost per inpatient day$_{considering\ DRG\ MIX}$). In this example, "performance data associated with ALOS" is an improvement factor that relates IT with ALOS, and can be extracted from the performance database (e.g., from a case study). Additionally, "$ALOS_{considering\ DRG\ MIX}$" and "Average variable cost per inpatient day$_{considering\ DRG\ MIX}$" is data of the average length of stay and average cost per day considering the diagnosis related groupings (DRG), respectively, and can be extracted from the healthcare profile 102. DRGs is a coding system used by healthcare providers to relevantly classify data. For example, data related to types of congenital heart diseases will be classified together in a DRG.

3. Patient Access

According to other studies, there is a correlation between satisfied patients and: (a) improved health outcomes, (b) reduced malpractice, (c) improved physician satisfaction, and (d) increased profitability. Given these benefits, health care providers are quite concerned with improving patient satisfaction. One key method by which to grow patient satisfaction includes improving patient access.

Patient access may be at the health system level or at the individual hospital/clinic level. Access at the health system level is largely affected by the availability of: (a) facilities (e.g. urban vs rural); (b) clinicians (i.e. healthcare labor shortage); and (c) technology (i.e. availability of the latest therapeutics). These inputs to the delivery of care are dependent upon government stability and political orientation and other factors such as economic development and country wealth. At the individual hospital/clinic level, patient access is generally associated with timely and affordable health care services for acute and chronic conditions as well as for emergency and preventive care. Aspects include the ability to respond in a timely manner to queries, the time taken to select physicians and schedule appointments, patient pre-processing time, on-line viewing and self management.

Access to care is limited by inefficient processes as well as by the lack of available staff; both of which also contribute to the high costs of delivering care. According to the-American Hospital Association workforce shortages have contributed to emergency room overcrowding and diversions decreased patient satisfaction, and reductions in the number of staffed beds. Internet enabled processes such as scheduling, billing, medical information management, prescribing and renewing prescriptions, patient education, and others all improve patient access outside the organization.

4. Staff Productivity

These are criteria for solutions that lead to improve elements in resource utilization and reduction in inefficiencies. There is a tremendous amount of interest in improving healthcare labor productivity. This stems from an industry labor shortage and the high overall cost of delivering care. The two key ways to improve labor productivity involve generating gains in staff efficiency and changing system processes. Measuring clinician productivity includes indications of clinician time spent providing direct patient care and performance of indirect patient care activities. Other performance indicators include measurement of the number of patients seen.

While more patients being treated may result in greater patient access and provider revenue, more clinician time with patients may result in better quality of care and labor satisfaction. In either case, improving productivity is a high industry priority.

Examples of performance indicators in IT benefit calculations associated with staff productivity are overtime reduction, form elimination, and document storage cost reduction. These performance indicators may be calculated in a variety of ways.

For example, overtime reduction can be calculated as follows: (performance data associated with overtime)×(overtime expenditure per 1000 admissions)×(total number of admissions/1000). In this example, "performance data associated with overtime" is an improvement factor that relates IT with overtime, and can be extracted from the performance database (e.g., from a case study). Moreover, "overtime expenditure per 1000 admissions" and "total number of admissions/1000" are normalized characteristic values that can be extracted from the healthcare profile 102.

Similarly, form elimination can be calculated as follows: (performance data associated with forms)×(form expenditure per 1000 admissions)×(total number of admissions/1000). In this case, "performance data associated with forms" is an improvement factor that relates IT with reduction of forms, and can be extracted from the performance database (e.g., from a case study). Furthermore, "form expenditure per 1000 admissions" and "total number of admissions/1000", are normalized characteristic values that can be extracted from the healthcare profile 102.

In another example, document storage cost reduction can be calculated as follows: (performance data associated with document storage and retrieval)×(document storage and retrieval expenditure per 1000 admissions)×(total number of admissions/1000). In this example, "performance data associated with document storage and retrieval" is an improvement factor that relates IT with reduction in cost for document storage and retrieval, and can be extracted from the performance database (e.g., from a case study). Additionally, "document storage and retrieval expenditure per 1000 admissions" and "total number of admissions/1000" are normalized characteristic values that can be extracted from the healthcare profile 102.

Additionally, some performance indicators may be relevant in evaluating several healthcare drivers. For example, form elimination and document storage cost reduction may be relevant to staff productivity, as well as cost optimization.

5. Staff Satisfaction

While there is broad consensus that there is a global healthcare workforce shortage, the severity of the shortage can vary widely depending upon an area's level of economic development. World Health Organization data indicate that Africa and Asia have the most need as measured by healthcare workers per 1,000 people. Similarly, there is a lack of adequate staff in rural areas compared to cities in both rich and poorer countries. Not only are there not enough doctors or nurses, but there are also noted shortages of pharmacists, laboratory technicians, other skilled medical professionals.

Without an adequate pool of healthcare workers, "prevention and treatment of disease and advances in health care cannot reach those in need". Recent studies point to the connection between adequate levels of registered nurse staffing and safe patient care. In the US, for example, the current situation is such that California has even mandated minimum patient to nurse ratios in hospitals. With the labor shortage, the healthcare industry is increasingly concerned with making their workforce as productive as possible as well as retaining what labor they have and potentially even improving their workforce through recruiting. In many countries hospitals struggle with high turnover and vacancy rates which affect access to health care. Given high replacement costs, opportunities to improve clinician satisfaction and retention are growing in importance.

According to one survey, key issues for nurses include low staffing levels, excessive over-time demands, perceptions of the quality of patient care, and support from co-workers and supervisors. Similarly, physician satisfaction also tends to be associated with the quality of care and work load, as well as pay, practice type, and level of autonomy.

Examples of performance indicators in IT benefit calculations associated with staff satisfaction are staff retention and emergency department patients leaving without treatment. This performance indicator may be calculated in a variety of ways.

For example, the benefit associated with staff retention can be calculated as follows: (performance data associated with staff retention)×(clinical staff replacement cost)×(clinical staff turnover rate). In this case, "performance data associated with staff retention" is an improvement factor that relates IT with staff retention, and can be extracted from the performance database (e.g, from a case study). Moreover, "clinical staff replacement cost" and "clinical staff turnover rate" are characteristic values that can be extracted from the healthcare profile 102.

In another example, the benefit associated with emergency department patients leaving without treatment (ED LWOTS) can be calculated as follows: (performance data associated with ED LWOTS)×(percentage of ED visitors LWOT)×(number of ED visitors)×(average net revenue per ED visitor) In this example, "performance data associated with ED LWOTS" is an improvement factor that relates IT with ED LWOTS, and can be extracted from the performance database (e.g, from a case study). Moreover, "percentage of ED visitors LWOT", "number of ED visitors", and "average net revenue per ED visitor" are characteristic values that can be extracted from the healthcare profile 102.

6. Revenue Enhancement

Revenue enhancement is largely a concern in areas where the providers of care are generally not government owned and or administrated. With some exceptions, American health providers are compensated for their services, in whole or in part, by insurance companies, the US government, or the patients themselves. In the hospital setting, revenue is largely dependent upon inpatient occupancy levels, and the clinicians' medical and ancillary services ordered and/or provided to patients. In the clinic, the volume of outpatient procedures is the key determinant of revenue. In hospital and clinic settings, charges, payment and reimbursement rates for patient services may vary widely depending on the type of service and even the geographic location.

Providers can grow revenue in several ways. Providers may expand through building or acquiring facilities in a different geographic area. New markets may also be entered by modifying existing facilities and offering new services such as imaging or cardiac surgery centers. Alternatively providers can enhance their revenue through improved facility and equipment utilization. Utilization is affected by a number of factors including facility reputation, the number and quality of the healthcare professionals providing care, the population size of the market being served, and the degree of competition.

Revenue cycle management is one notable industry trend that helps providers to further enhance their revenue by optimizing the patient billing process. The revenue cycle involves evaluating. a patient's insurance eligibility for services, capturing and submitting of charges for services rendered, and accounts receivable tracking. The key benefits of revenue cycle management include: (a) incremental revenue from improved charge capture and coding; (b) cash flow acceleration from reducing the time from service delivery to reimbursement; and even (c) lower costs of collection.

An example of a performance indicator in an IT benefit calculation associated with revenue enhancement may be "days in accounts receivable (AR) reduction." This performance indicator may be calculated in a variety of ways.

For example, the benefit associated with "days in accounts receivable reduction" can be calculated as follows: (performance data associated with AR reduction) ×(value per average customer accounts receivable day). In this example, "performance data associated with AR reduction" is an improvement factor that relates IT with AR days, and can be extracted from the performance database (e.g, from a case study). Additionally, "value per average customer accounts receivable day" is a normalized characteristic value that can be extracted from the healthcare profile 102.

7. Cost Optimization

The Health Industry is concerned with the rising costs of delivering care and the cost of risk and compliance. Overall costs of providing healthcare are on the rise. Since 1998, the "Hospital Market Basket"—an index that measures price inflation for the goods and services purchased by hospitals—has been growing significantly faster than the Consumer Price Index, a more general measure of inflation." While hospitals require drugs, medical devices, food, linen, and other supplies when treating patients, the most significant expenses are associated with paying labor wages and benefits. These can account for more than half of all provider expenses. Other significant expenditures include adoption of advances in medical technology. This may come in the form of new drugs, diagnostic equipment, surgical techniques, and medical devices. Despite the associated costs, health care providers continue to use technology to improve diagnosis, treatment, and overall patient outcomes.

Information technology can play a role in optimizing labor expenses, through the productivity improvements discussed previously. With greater productivity, access is improved with existing resources, and therefore the need for investment in additional staff and facilities may be lessened. Further, IT can improve patient safety and the overall quality of care through electronic records and clinical decision support. With better care, costs associated with high mortality rates and longer lengths of stay, as well as, medical liability can be reduced. With the better overall information management that comes with IT, hospitals can find additional benefits through reductions in scrap and waste through improved inventory management, lower costs of regulatory and quality reporting, and even better control systems that help avoid costs of fraud and theft.

Cost saving metrics refer to, highly quantifiable and tangible metrics. Typical examples are the elimination of storage charges related to hospital stock. Hardware costs are one of the largest and most pertinent costs. While unit costs of devices may be low, the volume required is likely to result in highly significant costs. Volume discounts should be incorporated into the negotiating process. Software costs are associated with the procurement of software to support applications, integration of department functions and importantly the development costs associated with the applications.

Examples of performance indicators in IT benefit calculations associated with cost optimization are be pharmacy cost reduction, form elimination, and document storage cost reduction. These performance indicators may be calculated in a variety of ways.

For example, the benefit associated with pharmacy cost reduction can be calculated as follows: (performance data associated with pharmacy cost reduction)×(pharmacy expenditure per 1000 admissions)×(total number of admissions/1000). In this case, "performance data associated with pharmacy cost reduction" is an improvement factor that relates IT with pharmacy cost reduction, and can be extracted from the performance database (e.g, from a case study). Moreover, "pharmacy expenditure per 1000 admissions" and "pharmacy expenditure per 1000 admissions" are normalized characteristic values that can be extracted from the healthcare profile 102.

As described above, form elimination and document storage cost reduction are examples of performance indicators that are relevant to a plurality of healthcare drivers.

Evaluation and Display of IT Impact on the Healthcare Industry

The evaluation of the first or second specification determined in step 204 or 208 of the method 200 may be displayed visually, as illustrated in FIG. 6A. The specification comprising a healthcare profile 102, a technology profile 104, and performance data 106 is evaluated to determine system performance values, such as a cost/benefit analysis 108 and 110, ROI 114, NPV 112, and IRR 116. The NPV 602, the ROI 604, and the IRR 606 may be presented visually. The benefits may be shown graphically, such as a pie chart as in 608 broken down by healthcare drivers.

Additionally, the evaluation may include some input and assumption values from the healthcare profile 102, the technology profile 104, and the performance data 106 along with evaluation data, such as associated cost 108 and benefits 110. Certain embodiments of the evaluation are illustrated in FIG. 7. The hospital profile 702, solution cost estimation 704, the performance data under the health driver patient safety related to fewer adverse drug events 706, and the performance data under the health care driver patient safety related to few medication-related legal claims 708 are illustrated. The performance data is displayed within the proper health driver category. For example, the annual benefit from fewer medication errors 710 as related to fewer adverse drug events 706 is presented to the user. The annual benefit from few malpractice claims 712 is presented under the few medication-related legal claims 708.

Similarly, some of the performance data and evaluation data under the healthcare driver quality of care are illustrated in FIG. 8. Saving from better care 802, revenue improvement 804, and cost savings from reporting 806 as related to quality of care may be displayed in the evaluation. Likewise, the healthcare driver patient satisfaction performance data related to few patients leaving without being seen 808 may be displayed in the evaluation.

Healthcare profile, technology profile, performance data, and evaluation data may be presented organized by other healthcare drivers as a portion of the evaluation of the specification from steps 204 and 208 of the method 200, as illustrated in FIG. 9. For example, under the healthcare driver under staff productivity, data is presented related to less overtime expenditure 902, and lower cost of managing paper 904. Data related to lower staff replacement costs associated with the healthcare driver staff satisfaction 906 may be presented in the evaluation. Similarly, evaluation data is organized by other health care drivers (908, 910, 912).

Figure 10:
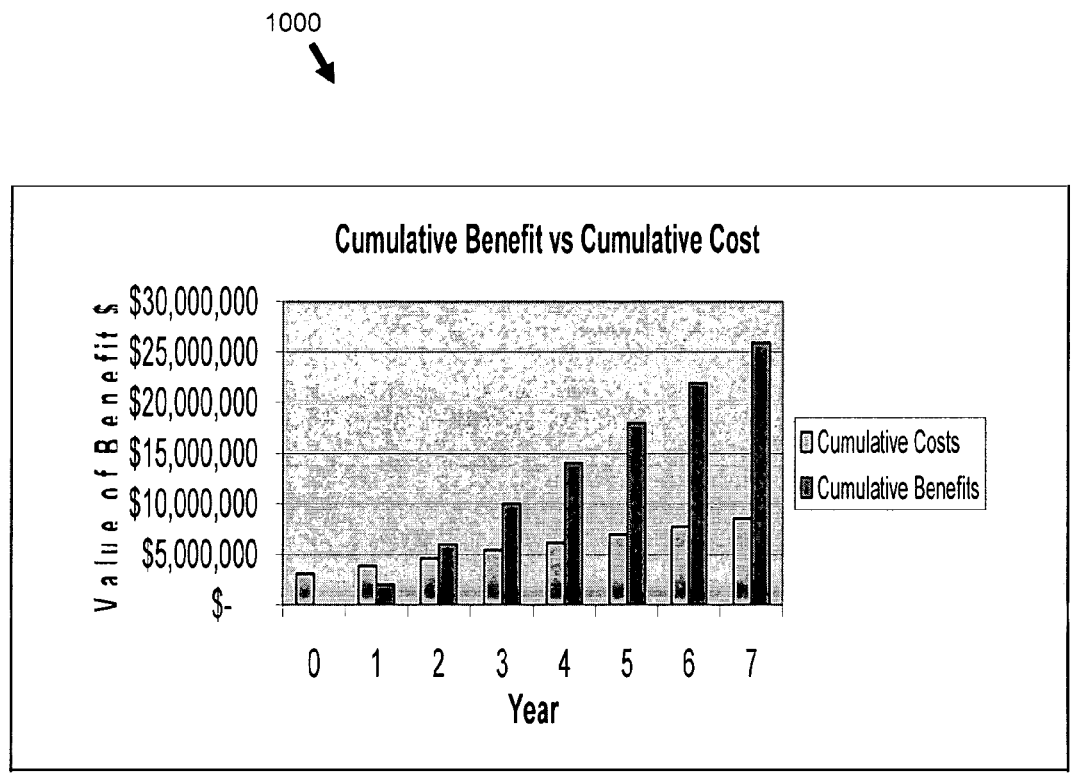
FIG. 10 shows an exemplary graphical representation for cost vs. benefit of an evaluation according to an embodiment of the present invention.

In addition, the evaluation of the specification may include a visual display of cumulative benefit vs. cumulative cost as illustrated in FIG. 10.

FIG. 11 illustrates the evaluation determined in steps 204 and 208 of the method 200, including a projection of yearly costs 1102 and yearly benefits 1104 for a number of years. As shown in FIG. 12, annual returns for a number of years 1202 may be calculated and presented in the evaluation, as well as yearly calculations for the NPV 1204, ROI 1206, and IRR 1208.

Conclusion

Additional embodiments relate to an apparatus (e.g., the system 100) for carrying out any one of the above-described methods, where the apparatus may include a computer for executing computer instructions related to the method. In this context the computer may be a general-purpose computer including, for example, a processor, memory, storage, and input/output devices (e.g., monitor, keyboard, disk drive, Internet connection, etc.). However, the computer may include circuitry or other specialized hardware for carrying out some or all aspects of the method. In some operational settings, the apparatus may be configured as a system that includes one or more units, each of which is configured to carry out some aspects of the method either in software, in hardware or in some combination thereof.

Figure 13:
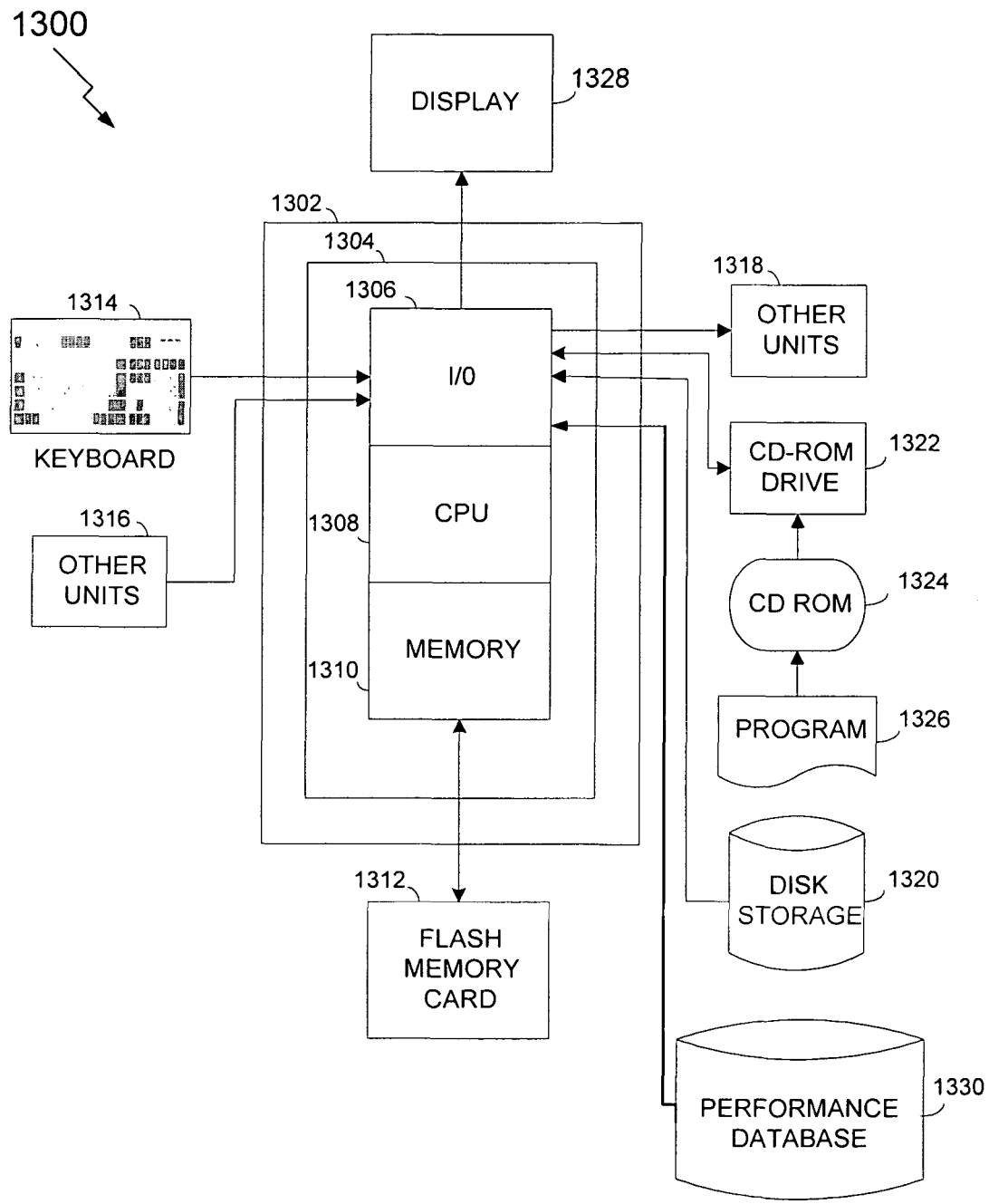
FIG. 13 shows a typical general purpose computer as applied to an embodiment of the present invention.

The system 100, for example, can be developed from conventional computer components. FIG. 13 shows a typical general purpose computer 1300 with a number of standard components that may be used for implementing the method 200. The main system 1302 includes a motherboard 1304 having an input/output ("I/O") section 406, one or more central processing units ("CPU") 1308, and a memory section 1310, which may have a flash memory card 1312 related to it. The I/O section 1306 is connected to a display 1328, a keyboard 1314, other similar general-purpose computer units 1316, 1318 (e.g., a network connection), a disk storage unit 1320 and a CD-ROM drive unit 1322. The CD-ROM drive unit 1322 can read a CD-ROM medium 1334 which typically contains programs 1326 and other data. Logic circuits or other components of these programmed computers will perform series of specifically identified operations associated with customers, merchants, and value-account systems.

At least some values based on the results of the method can be saved for subsequent use. For example the outputs of the system, including the ROI 114, NPV 112, IRR 116, and cost/benefit analysis 108, 110 can be saved directly for application as in memory (e.g, RAM (Random Access Memory)) or other form of disk storage 1320. A performance database 1330 may also be a data input to the system. Alternatively, some derivative or summary form of the results (e.g., averages, interpolations, etc.) can be saved for later use according to the requirements of the operational setting.

Additional embodiments also relate to a computer-readable medium that stores (e.g., tangibly embodies) a computer program for carrying out any one of the above-described methods by means of a computer. The computer program may be written, for example, in a general-purpose programming language (e.g., Excel, C, C++) or some specialized application-specific language. The computer program may be stored as an encoded file in some useful format (e.g., binary, ASCII) that may be used in a spreadsheet application like Excel, for example.

Figure 14:
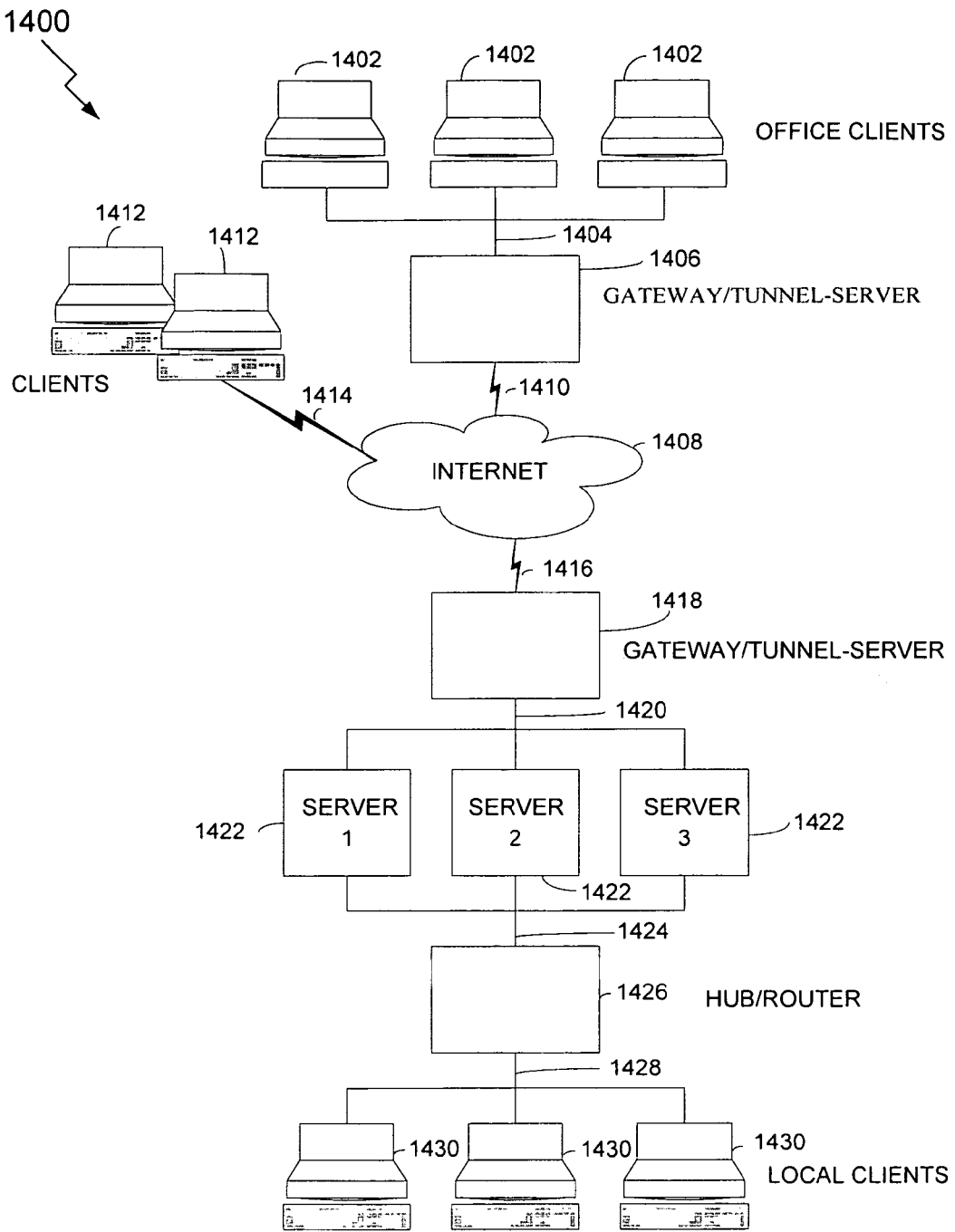
FIG. 14 shows a typical Internet network configuration as applied to the present invention.

The added computer units 1316, 1318 can be connected through a network system. Some of the elements of a typical Internet network configuration 1400 are shown in FIG. 14, where a number of office client machines 1402, possibly in a branch office of an enterprise, are shown connected 1404 to a gateway/tunnel-server 1406 which is itself connected to the Internet 1408 via some internet service provider (ISP) connection 1410. Also shown are other possible clients 1412 similarly connected to the internet 1408 via an ISP connection 1414. An additional client configuration is shown for local clients 1430 (e.g., in a home office). An ISP connection 1416 connects the Internet 1408 to a gateway/tunnel-server 1418 that is connected 1420 to various enterprise application servers 1422. These servers 1422 are connected 1424 to a hub/router 1426 that is connected 1428 to various local clients 1430. For example, the system 100 can be implemented at a server 1422 that is accessible through multiple local clients 1430.

Although only certain exemplary embodiments of this invention have been described in detail above, those skilled in the art will readily appreciate that many modifications are possible in the exemplary embodiments without materially departing from the novel teachings and advantages of this invention. For example, aspects of embodiments disclosed above can be combined in other combinations to form additional embodiments. Accordingly, all such modifications are intended to be included within the scope of this invention.

What is claimed is:

1. A computer-implemented method of evaluating a healthcare information system, the computer-implemented method comprising executing the following acts with a microprocessor:
   determining, using the microprocessor, a first specification for the healthcare information system, wherein the first specification includes healthcare profile data for specifying a profile of a healthcare provider, technology profile data for specifying a profile of technology resources, and performance data for measuring benefits associated with performance indicators of the healthcare information system;
   determining, using the microprocessor, a first evaluation of the first specification for the healthcare information system, wherein the first evaluation includes system performance values;
   presenting, using the microprocessor, at least some characteristic values for the performance indicators to a user for changing the first specification;
   specifying, using the microprocessor, a user input for changing at least some values of the first specification for the healthcare information system to provide a second specification for the healthcare information system;
   determining, using the microprocessor, a second evaluation of the second specification for the healthcare information system, wherein the second evaluation includes system performance values; and
   arriving at a performance analysis of the healthcare information system by comparing, using the microprocessor, the first evaluation and the second evaluation.

2. The computer-implemented method according to claim 1, wherein the healthcare profile data includes values for hospital operations, hospital financial information, and a hospital profile.

3. The computer-implemented method according to claim 1, wherein the technology profile data includes values for costs associated with hardware and software, costs for software licenses, and number of users.

4. The computer-implemented method according to claim 1, wherein the performance indicators include average cost per admission and cost of medication claims.

5. The computer-implemented method according to claim 1, wherein determining the performance data includes extracting values from a healthcare performance database that includes values from at least one case study for evaluating healthcare based on information technology.

6. The computer-implemented method according to claim 1, wherein determining the performance data includes extracting values from a healthcare performance database that includes values from at least one case study for evaluating healthcare based on healthcare activities.

7. The computer-implemented method according to claim 1, wherein the evaluation for each specification of the healthcare system includes values for at least one of cost, benefit, NPV (net present value), IRR (initial rate of return), and ROI (return on investment).

8. The computer-implemented method according to claim 1, wherein the characteristic values for the performance indicators include a nominal value and a range of values based on a healthcare performance database.

9. The computer-implemented method according to claim 8, wherein the healthcare performance database includes values from at least one case study for evaluating healthcare based on healthcare activities.

10. The computer-implemented method according to claim 8, wherein the healthcare performance database includes values from at least one case study for evaluating healthcare based on information technology.

11. The computer-implemented method according to claim 1, further comprising:
determining, using the microprocessor, a plurality of healthcare drivers that characterize qualitative goals of the healthcare information system; and
associating, using the microprocessor, each performance indicator with a corresponding healthcare driver.

12. The computer-implemented method according to claim 11, wherein at least one healthcare driver is selected from the group consisting of: patient safety, quality of care, patient satisfaction, staff productivity, staff satisfaction, revenue enhancement, and cost optimization.

13. The computer-implemented method according to claim 11, wherein specifying the user input includes selecting a healthcare driver and a corresponding performance indicator.

14. The computer-implemented method according to claim 1, wherein changing at least some values of the second specification improves the system performance values of the evaluation.

15. The computer-implemented method according to claim 1, wherein the evaluation comprises a categorization by each health driver.

16. The computer-implemented method according to claim 1, wherein the evaluation comprises at least one graphical display.

17. The computer-implemented method according to claim 1, wherein the evaluation comprises at least one arithmetic combination of performance data, a normalized expense, and a normalized admission number.

18. The computer-implemented method according to claim 1, wherein the first specification is the same as the second specification.

19. An apparatus for determining an evaluation of a healthcare information system, the apparatus comprising a computer for executing computer instructions, wherein the computer includes computer instructions for:
determining a first specification for the healthcare information system, wherein the first specification includes healthcare profile data for specifying a profile of a healthcare provider, technology profile data for specifying a profile of technology resources, and performance data for measuring benefits associated with performance indicators of the healthcare information system;
determining a first evaluation of the first specification for the healthcare information system, wherein the first evaluation includes system performance values;
presenting at least some characteristic values for the performance indicators to a user for changing the first specification;
specifying a user input for changing at least some values of the first specification for the healthcare information system to provide a second specification for the healthcare information system;
determining a second evaluation of the second specification for the healthcare information system, wherein the second evaluation includes system performance values; and
arriving at a performance analysis of the healthcare information system by comparing, using the microprocessor, the first evaluation and the second evaluation.

20. The apparatus according to claim 19, wherein the computer includes a processor with memory for executing at least some of the computer instructions.

21. The apparatus according to claim 19, wherein the computer includes circuitry for executing at least some of the computer instructions.

22. The apparatus according to claim 19, wherein the computer further includes computer instructions for:
determining a plurality of healthcare drivers that characterize qualitative goals of the healthcare information system; and
associating each performance indicator with a corresponding healthcare driver.

23. A non-transitory computer-readable medium that stores a computer program for determining an evaluation of a healthcare information system, wherein the computer program includes instructions for:
determining a first specification for the healthcare information system, wherein the first specification includes healthcare profile data for specifying a profile of a healthcare provider, technology profile data for specifying a profile of technology resources, and performance data for measuring benefits associated with performance indicators of the healthcare information system;
determining a first evaluation of the first specification for the healthcare information system, wherein the first evaluation includes system performance values;
presenting at least some characteristic values for the performance indicators to a user for changing the first specification;
specifying a user input for changing at least some values of the first specification for the healthcare information system to provide a second specification for the healthcare information system;
determining a second evaluation of the second specification for the healthcare information system, wherein the second evaluation includes system performance values; and
arriving at a performance analysis of the healthcare information system by comparing, using the microprocessor, the first evaluation and the second evaluation.

24. The non-transitory computer-readable medium according to claim 23, wherein the computer program further includes instructions for:
determining a plurality of healthcare drivers that characterize qualitative goals of the healthcare information system; and
associating each performance indicator with a corresponding healthcare driver.

25. An apparatus for determining an evaluation of a healthcare information system, the apparatus comprising a computer for executing computer instructions, wherein the computer includes computer instructions for:
determining a first specification for the healthcare information system, wherein the first specification includes healthcare profile data for specifying a profile of a healthcare provider, technology profile data for specifying a profile of technology resources, and performance data for measuring benefits associated with performance indicators of the healthcare information system;

determining a first evaluation of the first specification for the healthcare information system, wherein the first evaluation includes system performance values;

receiving a change for at least some values of the first specification for the healthcare information system to provide a second specification for the healthcare information system;

determining a second evaluation of the second specification for the healthcare information system, wherein the second evaluation includes system performance values; and arriving at a performance analysis of the healthcare information system by comparing, using the microprocessor, the first evaluation and the second evaluation.

26. The computer-implemented method according to claim 1, wherein the performance indicators include a value of staff affected by adverse drug events.

27. The apparatus according to claim 19, wherein the performance indicators include a value of staff affected by adverse drug events.

28. The non-transitory computer-readable medium according to claim 23, wherein the performance indicators include a value of staff affected by adverse drug events.

29. The apparatus according to claim 25, wherein the performance indicators include a value of staff affected by adverse drug events.

* * * * *